(12) United States Patent
Hart et al.

(10) Patent No.: US 6,958,051 B2
(45) Date of Patent: Oct. 25, 2005

(54) DUAL BALLOON VALVE CONTROL WITH PRESSURE INDICATOR

(75) Inventors: Colin P. Hart, Queensbury, NY (US); Thomas Deyette, Jr., Hudson Falls, NY (US); Glenn H. Wadleigh, Queensbury, NY (US)

(73) Assignee: SciMed Life Systems, Inc., Maple Grove, MN (US)

( * ) Notice: Subject to any disclaimer, the term of this patent is extended or adjusted under 35 U.S.C. 154(b) by 361 days.

(21) Appl. No.: 10/021,517

(22) Filed: Oct. 29, 2001

(65) Prior Publication Data

US 2003/0079752 A1 May 1, 2003

(51) Int. Cl.$^7$ ............................................... A61M 29/00
(52) U.S. Cl. ........................................ 604/96; 604/533
(58) Field of Search ................................ 128/887, 888; 606/108, 127, 192; 604/5, 9, 96, 101

(56) References Cited

U.S. PATENT DOCUMENTS

| | | | |
|---|---|---|---|
| 3,211,150 A | 10/1965 | Foderick | |
| 4,753,238 A | 6/1988 | Gaiser | |
| 4,911,163 A | * 3/1990 | Fina | ........................... 606/127 |
| 5,669,879 A | 9/1997 | Duer | |
| 6,017,324 A | * 1/2000 | Tu | ............................... 604/96 |
| 6,179,815 B1 | 1/2001 | Foote | |
| 6,238,382 B1 | * 5/2001 | Schock | ....................... 604/533 |

FOREIGN PATENT DOCUMENTS

| | | |
|---|---|---|
| EP | 0 299 158 A1 | 1/1989 |
| EP | 0 299 158   * | 1/1989 |
| EP | 0 988 870 A2 | 3/2000 |
| EP | 0 988 870 A3 | 7/2000 |
| FR | 2 803 532 | 1/2000 |

* cited by examiner

*Primary Examiner*—Michael Brown
(74) *Attorney, Agent, or Firm*—Crompton, Seager & Tufte LLC

(57) ABSTRACT

The present invention is drawn to a valve control accessory for use with a dual balloon stent delivery catheter. The accessory device includes a bifurcated fluid line adapted to connect to an inflation device using a proximal luer connector. Additional luer connectors at the distal ends of the main fluid line and branched fluid line are engaged to connect to the proximal ends of a bifurcated catheter shaft, allowing the fluid lines to be in fluid communication with a parent and sidebranch balloon respectively. In one embodiment, stopcocks are formed in both the main and sidebranch fluid lines to allow independent or simultaneous expansion of each balloon. A pressure indicator may be placed on either fluid line to indicate which line is under pressure.

18 Claims, 2 Drawing Sheets

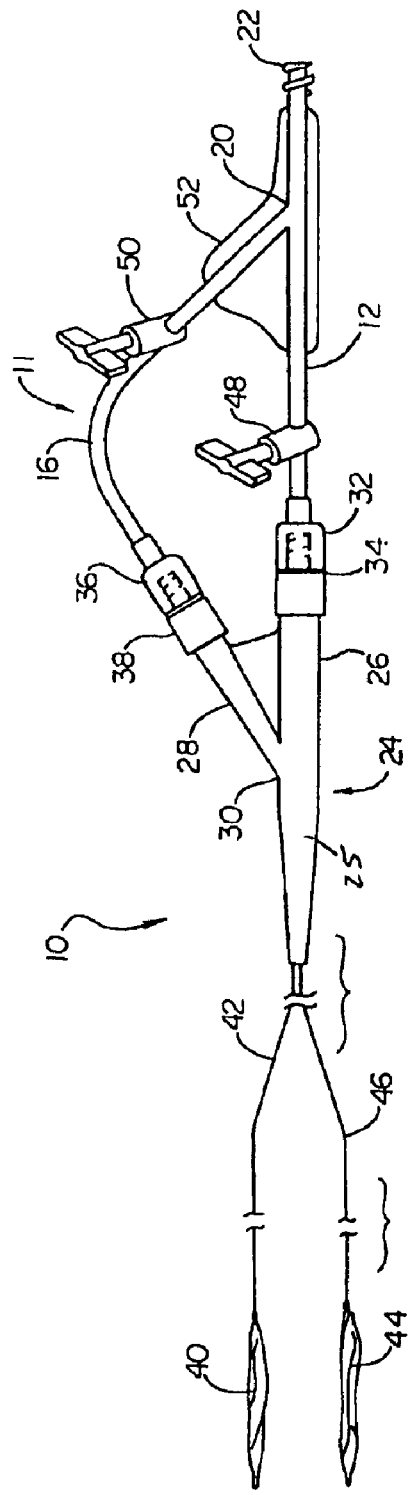

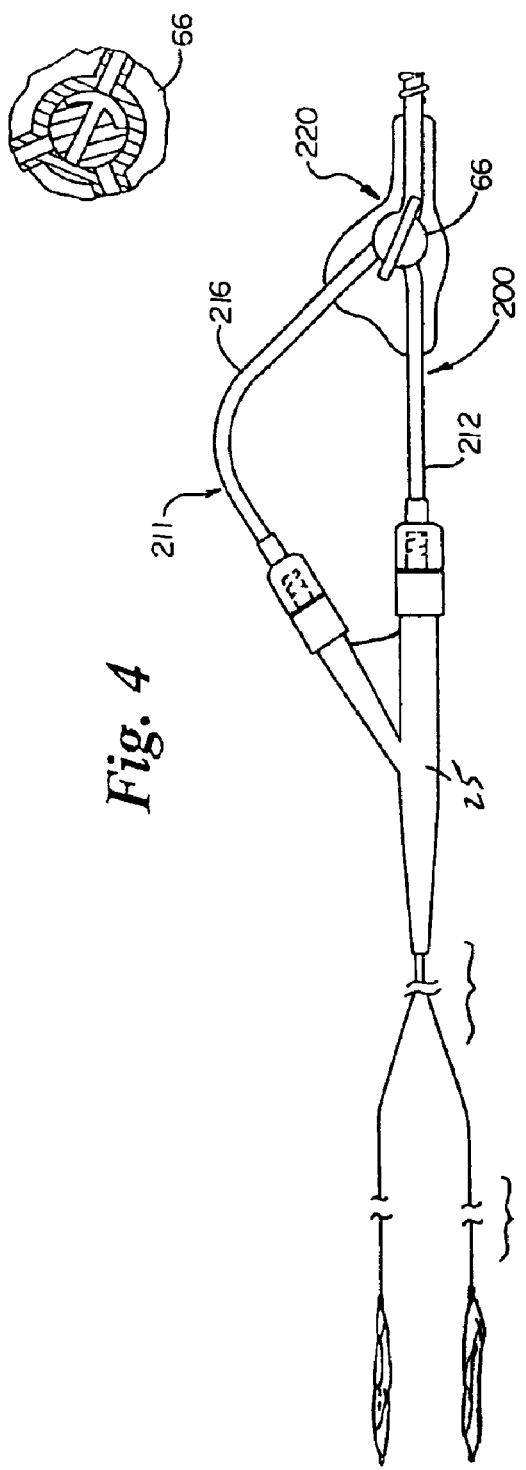

DUAL BALLOON VALVE CONTROL WITH PRESSURE INDICATOR

BACKGROUND OF THE INVENTION

The present invention relates to a system for use in the treatment of vascular disease. Vascular disease is a common condition which causes the development of a stenosis, or narrowing, of the vasculature. The resulting reduction in blood circulation in the stenotic vessel may cause a variety of medical problems.

A common treatment of stenosis involves the delivery of a stent via a delivery device, such as a catheter, to the region of the stenosis. Stents are typically a tubular device which can be expanded from a first collapsed state to a second expanded state. The stent may be crimped down over a balloon which is disposed about a distal region of the catheter. The stent delivery catheter advances the stent to the delivery site, at which time the balloon is inflated, causing the stent to expand to its deployed state in which the stent engages the inner walls of the blood vessel, thereby maintaining the vessel in an unrestricted state.

Stenotic lesions may also form at a bifurcation, which is a region of the vasculature where a parent vessel is bifurcated into at least two branch vessels. Bifurcated lesions pose additional challenges for medical treatment. Such cases may require the deployment of two stents in the bifurcated region or, alternatively, a single stent have a first diameter portion for deployment in the parent vessel and a second diameter portion for deployment in the branch vessel.

To assist in the deployment of a bifurcated stent device for treatment of a bifurcation lesion, a specialized catheter can be used which may include a dual balloon stent deployment system. A parent balloon can deploy a first diameter portion of the stent in the parent vessel, while the sidebranch balloon can deploy a second stent diameter portion in a branch vessel. Each of the two balloons is in fluid communication with its own lumen. The lumens are connected to separate inflation devices which deliver inflation fluid through the lumens to inflate the balloons.

What would be desirable is a stent delivery catheter system in which the user could inflate both balloons separately and/or simultaneously without having to disconnect or reconnect the inflation device. It would also be desirable to have a means for indicating to the user which of the dual balloons is deflated at any given time.

SUMMARY OF THE INVENTION

The present invention pertains to a stent delivery catheter system with a dual balloon valve control and pressure indicator. In one embodiment, the system includes a dual balloon/dual inflation lumen catheter having an accessory device attached at its proximal end. The accessory device includes a single luer connection point for an inflation device, a bifurcated fluid line for delivering inflation fluid to each balloon separately, and two additional luer connection points which connect the accessory device to the inflation lumens in fluid communication with the parent and sidebranch balloons, respectively. The branch of the bifurcated fluid line which leads to the sidebranch balloon may extend at an angle from the branch which leads to the parent balloon. A one-way stopcock is mounted on the branch of the bifurcated fluid line connecting the inflation device with the parent balloon.

In a preferred embodiment, a second one-way stopcock is added to the branch of the fluid line leading to the sidebranch balloon. In yet another embodiment, the one-way stopcocks are replaced by a single 3-way stopcock placed at the bifurcation point of the accessory device fluid lines.

A pressure indicator may be placed on either or both of the fluid lines of the above embodiments. The indicator can show the user which of the balloons is deflated at any given time.

BRIEF DESCRIPTION OF THE DRAWINGS

FIG. 1 illustrates a dual balloon/dual inflation path stent delivery catheter including a dual balloon valve control accessory having a main fluid line and a branched fluid line with a stopcock;

FIG. 2 illustrates a cross-sectional view of a pressure indicator;

FIG. 3 illustrates a dual balloon valve control accessory for a dual balloon/dual inflation path stent delivery catheter having a main fluid line with a stopcock and a sidebranch fluid line;

FIG. 4 illustrates a dual balloon valve control accessory for a dual balloon/dual inflation path stent delivery cathether having a three-way stopcock located at the bifurcation point of the main and sidebranch fluid lines;

FIG. 5 illustrates a cross-sectional view of the three-way stopcock shown in FIG. 4 in which fluid is prevented from entering either fluid line;

FIG. 6 illustrates a cross-sectional view of the three-way stopcock shown in FIG. 4 in which fluid is allowed to enter either fluid line;

FIG. 7 illustrates a cross-sectional view of the three-way stopcock shown in FIG. 4 in which fluid is allowed to enter only a first fluid line; and FIG. 8 illustrates a cross-sectional view of the three-way stopcock shown in FIG. 4 in which fluid is allowed to enter only a second fluid line.

DETAILED DESCRIPTION

FIG. 1 illustrates a preferred embodiment of a dual balloon/dual inflation path stent delivery catheter system 10, including a valve control accessory device 11 and catheter 24. Accessory device 11 includes a main fluid line 12 and a sidebranch fluid line 16. Sidebranch fluid line 16 diverges from main fluid line 12 at bifurcation point 20. Main fluid line 12 includes a luer connection point 22 at its proximal end adapted to engage a source of inflation fluid. Catheter 24 includes a manifold 25 having a main shaft 26 and a sidebranch shaft 28. Sidebranch shaft 28 converges with main shaft 26 at bifurcation point 30.

A luer connection point 32 is located at the distal end of main fluid line 12 of accessory device 11, and is adapted to engage an opening 34 at the proximal end of main shaft 26. Luer connection point 36 is located at the distal end of sidebranch fluid line 16, and is adapted to engage opening 38 at the proximal end of sidebranch shaft 28.

A first one-way stopcock 48 is disposed about mainbranch 12 proximal to luer connection point 32. A second one-way stopcock 50 is disposed about sidebranch 16 proximal of luer connection point 36. Accessory device 11 may also include finger grip 52 disposed about bifurcation point 20, which makes valve control accessory 11 easier to hold by reducing the chance of having it spin in use.

A sidebranch balloon 40 is in fluid communication with sidebranch fluid line 16 of accessory device 11 through an inflation lumen disposed within tubular member 42. A parent balloon 44 is in fluid communication with main fluid line 12 of accessory device 11 through an inflation lumen disposed within tubular member 46.

The fluid lines of valve control accessory 11 can be flexible or rigid, and may be formed from any suitable material well known to those of skill in the art. Stopcocks 48 and 50 similarly may be formed from materials known to those of skill in the art.

In use, the catheter system of FIG. 1 allows the user to use one inflation device to inflate or deflate the balloons separately or simultaneously, without having to disconnect or reconnect the inflation device. Catheter 24 may be advanced through the vasculature to the site of a lesion in a bifurcated vessel such that the bifurcated stent is properly positioned within the bifurcated vessel.

Once the catheter is in position, stopcock 50 may be turned to the "open" position and a source of inflation fluid attached to luer connecter 22 is used to introduce fluid into inflation lumen 42, causing sidebranch balloon 40 to inflate, thereby expanding into its deployed position that portion of the stent that is in the sidebranch vessel. Inflating the sidebranch balloon 40 first serves to properly align the opening in the stent with the sidebranch vessel. Inflating the parent balloon without inflating the sidebranch balloon can be undesirable in that a portion of the stent could be deformed.

Sidebranch balloon 40 may then be deflated in order to temporarily restore blood flow through the sidebranch vessel. Next, stopcock 48 and stopcock 50 are both turned to the "open" position, such that inflation fluid may also flow through main fluid line 12 and into inflation lumen 46. Both sidebranch balloon 40 and parent balloon 44 are thereby inflated simultaneously so as to fully deploy the stent. Sidebranch balloon 40 and parent balloon 44 are then deflated simultaneously. Catheter 24 is then withdrawn, leaving the stent in place within the bifurcated vessel.

The presence of stopcocks on both the main fluid line 12 and the sidebranch fluid line 16 serves to isolate the parent balloon 44 from the sidebranch balloon 40, thereby providing the flexibility to allow the user to inflate and deflate each balloon in a variety of ways. For example, the balloons could be inflated to different pressures.

A significant feature of valve control accessory 11 is the branching off of sidebranch fluid line 16 from the main fluid line 12 in the shape of a "y." This provides an intuitive reminder to the user that the sidebranch fluid line 16 is in fluid communication with the sidebranch balloon 40. Such a configuration can reduce the chance of the user making an error with respect to which stopcock regulates inflation fluid flow to which balloon.

FIG. 2 illustrates a cross-sectional view of a preferred embodiment for a pressure indication device 54 which may be utilized in conjunction with all embodiments of the dual balloon valve control accessory of the present invention. Device 54 may be disposed on fluid line 12 distal of stopcock 48. Pressure indicator device 54 includes a housing 56 and a cap 58, which may be opaque. Cap 58 serves to securely hold the internal components of pressure indicator device 54 within the housing 56. An elastomeric component 60 is disposed within housing 56 and may be formed from any suitable elastomeric material. Pressure indicator device 54 also includes an opening 62 into inflation lumen 14 at its base. A diaphragm 64, which may be formed from any suitable elastomeric material, serves to prevent inflation fluid from lumen 14 from entering the inside of housing 56 via opening 62.

In use, the flow of inflation fluid through lumen 14 past pressure indicator device 54 subjects elastomeric diaphragm 64 to pressure, such that it flexes, causing the upward deformation of elastomeric component 60. The upward deformation causes elastomeric component 60 to protrude above the cap 58, as shown. The protrusion of elastomeric component 60 provides a visual indication to the user of the catheter that the catheter is under pressure. The protrusion also provides a tactile indicator of pressure in the form of an easily felt bump on the cap 58. When the inflation fluid is no longer under pressure, elastomeric diaphragm 64 relaxes and returns to its unflexed position, causing elastomeric diaphragm 64 to assume a non-deformed position such that elastomeric component 60 no longer protrudes from cap 58.

Generally, it is desired that both balloons be deflated before the catheter system is withdrawn from the vasculature. Since the embodiment of FIG. 1 allows each balloon to be inflated or deflated independently, the presence of pressure indicator 54 enhances the ability of the user to check whether both balloons are deflated before the catheter system is removed from the patient. Pressure indicator 54 may also be formed as a separate piece to be connected in-line on any device where pressure indication is desired.

FIG. 3 illustrates an alternative embodiment of a valve control accessory for a dual balloon/dual inflation path stent delivery catheter. Valve control accessory 111 is similar in most respects to valve control accessory 11 of FIG. 1 with regard to formation and use, except that no stopcock is present on sidebranch fluid line 116. Stopcock 148 is disposed about main fluid line 112. This embodiment allows the user to regulate the flow of inflation fluid through the main fluid line 112, but not the sidebranch fluid line 116. Since, as described above, the sidebranch balloon is generally desired to be inflated first during use, this configuration ensures that the sidebranch balloon will always be inflated before the parent balloon, so long as stopcock 148 is closed.

FIG. 4 illustrates yet another embodiment of the present invention. Valve control accessory 211 is similar to valve control accessory 11 of FIG. 1, except that a single three-way stopcock 66 at bifurcation point 220 replaces individual one-way stopcocks in the main fluid line 212 and sidebranch fluid line 216. Stopcock 66 can be formed from two mating core pins within a mold that would be pulled out in a parallel direction.

FIGS. 5–8 illustrate cross-sectional views of the various positioning possibilities of three-way stopcock 66. In FIG. 5, stopcock 66 is shown in the "off" position, in which inflation fluid is prevented from flowing through either main fluid line 212 or sidebranch fluid line 216. In FIG. 6, stopcock 66 is shown in the "on" position, in which inflation fluid is allowed to flow through either main fluid line 212 or sidebranch fluid line 216. FIG. 7 illustrates stopcock 66 in the "left on" position, in which inflation fluid is allowed to flow only through main fluid line 212. FIG. 8 illustrates stopcock 66 in the "right on" position, in which inflation fluid is allowed to flow only through the sidebranch fluid line 216.

It will be understood that this disclosure, in many respects, is only illustrative. Changes may be made in details, particularly in matters of shape, size, material, and arrangement of parts without exceeding the scope of the invention. For example, any of the embodiments above may be made as an integral part of an inflation device, making the connection between the line from the inflation device to the luer connector of the valve control accessory into a permanent, non-separable connection. Additionally, an inflation device could be manufactured with two flexible parallel lines permanently attached to the distal end of the inflation device's barrel. Luer connection points would be placed on the distal ends of the lines for connecting to the balloons. Stopcocks could be placed in just one line, between the barrel and a distal luer connection point, or in both lines. Also, the bifurcated fluid lines of the valve control accessory device may assume a configuration different from the "y" shape illustrated in FIG. 1 and FIG. 3. For example, the bifurcation may be symmetrically shaped. Accordingly, the scope of the present invention is as defined in the language of the claims.

What is claimed is:

1. A dual balloon valve control accessory device designed for use with a stent delivery catheter comprising:
    a bifurcated tubular member defining a first fluid line and a second fluid line, the first fluid line comprising a proximal end adapted to connect to a source of inflation fluid and a distal end adapted to connect to a first shaft of a bifurcated catheter, and the second fluid line comprising a proximal end and a distal end adapted to connect to a second shaft of the bifurcated catheter, the second fluid line being in fluid communication with the first fluid line at a bifurcation point located at the proximal end of the second fluid line.

2. The dual balloon valve control accessory of claim 1, additionally comprising a finger grip disposed about the bifurcation point adapted to make the accessory easier to hold.

3. The dual balloon valve control accessory of claim 1, additionally comprising a one-way stopcock disposed about the first fluid line between its proximal end and its distal end and adapted to control the flow of fluid through the first fluid line.

4. The dual balloon valve control accessory of claim 1, additionally comprising a one-way stopcock disposed about the second fluid line between its proximal and distal ends, and adapted to control the flow of fluid through the second fluid line.

5. The dual balloon valve control accessory of claim 1, additionally comprising:
    a first one-way stopcock disposed about the second fluid line and adapted to control the flow of fluid through the second fluid line; and
    a second one-way stopcock disposed about the first fluid line and adapted to control the flow of fluid through the first fluid line.

6. The dual balloon valve control accessory of claim 1, additionally comprising a three-way stopcock disposed about the bifurcation point and adapted to control the flow of fluid through the first fluid line and the second fluid line.

7. The dual balloon valve control accessory of claim 1, additionally comprising a pressure indicator disposed about the first fluid line.

8. The dual balloon valve control accessory of claim 1, additionally comprising a pressure indicator disposed about the second fluid line.

9. The dual balloon valve control accessory of claim 1, additionally comprising a first pressure indicator disposed about the first fluid line and a second pressure indicator disposed about the second fluid line.

10. A system for delivering a bifurcated stent comprising:
    a bifurcated tubular member defining a first fluid line and a second fluid line, the first fluid line comprising a proximal end adapted to connect to a source of inflation fluid and a distal end adapted to connect to a main shaft of a bifurcated catheter, and the second fluid line comprising a proximal end and a distal end adapted to connect to a sidebranch shaft of a bifurcated catheter, the second fluid line being in fluid communication with the first fluid line at a bifurcation point located at the proximal end of the second fluid line;
    a bifurcated elongate catheter member including a main shaft having a distal end and a proximal end connected to the distal end of the main fluid line of the valve control accessory, and a sidebranch shaft having a proximal end connected to the distal end of the sidebranch fluid line;
    a first balloon disposed about a distal region of the main shaft and in fluid communication with the first fluid line via a first inflation lumen;
    a second balloon disposed about a distal region of the main shaft and in fluid communication with the second fluid line via a second inflation lumen;
    a first portion of a stent disposed about the first balloon; and
    a second portion of a stent disposed about the second balloon.

11. The system of claim 10, additionally comprising a finger grip disposed about the bifurcation point adapted to make the accessory easier to hold.

12. The system of claim 10, additionally comprising a one-way stopcock disposed about the first fluid line between its proximal end and its distal end and adapted to control the flow of fluid through the first fluid line.

13. The system of claim 10, additionally comprising a one-way stopcock disposed about the second fluid line between its proximal and distal ends, and adapted to control the flow of fluid through the second fluid line.

14. The system of claim 10, additionally comprising a first one-way stopcock disposed about the first fluid line and adapted to control the flow of fluid through the first fluid line and a second one-way stopcock disposed about the second fluid line and adapted to control the flow of fluid through the second fluid line.

15. The system of claim 10, additionally comprising a three-way stopcock disposed about the bifurcation point and adapted to control the flow of fluid through the first fluid line and the second fluid line.

16. The system of claim 10, additionally comprising a pressure indicator disposed about the first fluid line.

17. The system of claim 10, additionally comprising a pressure indicator disposed about the second fluid line.

18. The system of claim 10, additionally comprising a first pressure indicator disposed about the first fluid line and a second pressure indicator disposed about the second fluid line.

* * * * *